(12) United States Patent
Runcie

(10) Patent No.: US 8,530,826 B2
(45) Date of Patent: Sep. 10, 2013

(54) AUTOMATED SHUTTER FOR DARK ACCLIMATING SAMPLES

(76) Inventor: John W. Runcie, Umina Beach (AU)

( * ) Notice: Subject to any disclaimer, the term of this patent is extended or adjusted under 35 U.S.C. 154(b) by 309 days.

(21) Appl. No.: 12/921,445

(22) PCT Filed: Mar. 13, 2009

(86) PCT No.: PCT/AU2009/000295
§ 371 (c)(1),
(2), (4) Date: Nov. 15, 2010

(87) PCT Pub. No.: WO2009/111834
PCT Pub. Date: Sep. 17, 2009

(65) Prior Publication Data
US 2011/0101210 A1    May 5, 2011

(30) Foreign Application Priority Data
Mar. 14, 2008 (AU) .................................. 2008901267

(51) Int. Cl.
*G01N 21/64* (2006.01)
*G01N 21/01* (2006.01)
(52) U.S. Cl.
USPC .................. 250/237 R; 250/461.2; 435/292.1

(58) Field of Classification Search
USPC ................... 250/237 R, 458.1, 461.1, 461.2; 435/287.2, 289.1, 292.1, 293.1
See application file for complete search history.

(56) References Cited

U.S. PATENT DOCUMENTS

| | | | | |
|---|---|---|---|---|
| 3,787,703 | A | * | 1/1974 | Topol ............................. 250/574 |
| 4,319,842 | A | * | 3/1982 | Priarone et al. ............... 356/317 |
| 4,643,571 | A | * | 2/1987 | Ferber et al. .................. 356/326 |
| 5,014,225 | A | * | 5/1991 | Vidaver et al. ................. 702/19 |
| 7,083,975 | B2 | * | 8/2006 | Green et al. ................ 435/289.1 |
| 2003/0007086 | A1 | * | 1/2003 | Bean et al. ..................... 348/363 |
| 2003/0148502 | A1 | * | 8/2003 | Green et al. .............. 435/287.2 |
| 2007/0037274 | A1 | * | 2/2007 | Green et al. .............. 435/287.2 |
| 2011/0101210 | A1 | * | 5/2011 | Runcie ...................... 250/237 R |

* cited by examiner

*Primary Examiner* — John Lee
(74) *Attorney, Agent, or Firm* — Neal Blibo LLC

(57) ABSTRACT

An automated shutter for dark acclimating a sample, comprising a base and a head mounted to the base and movable between an open and closed position. The automated shutter further comprises one or more artificial light sources and one or more optical detectors disposed in said head or base, and wherein the head is contiguous with the sample when moved into the closed position. Another embodiment comprises an enclosure placed over a sample to be dark acclimatized, with one or more artificial light sources and optical detectors disposed within or closely adjacent to said enclosure which is configured to be transformed between an optically transparent state and an optically opaque state.

24 Claims, 6 Drawing Sheets

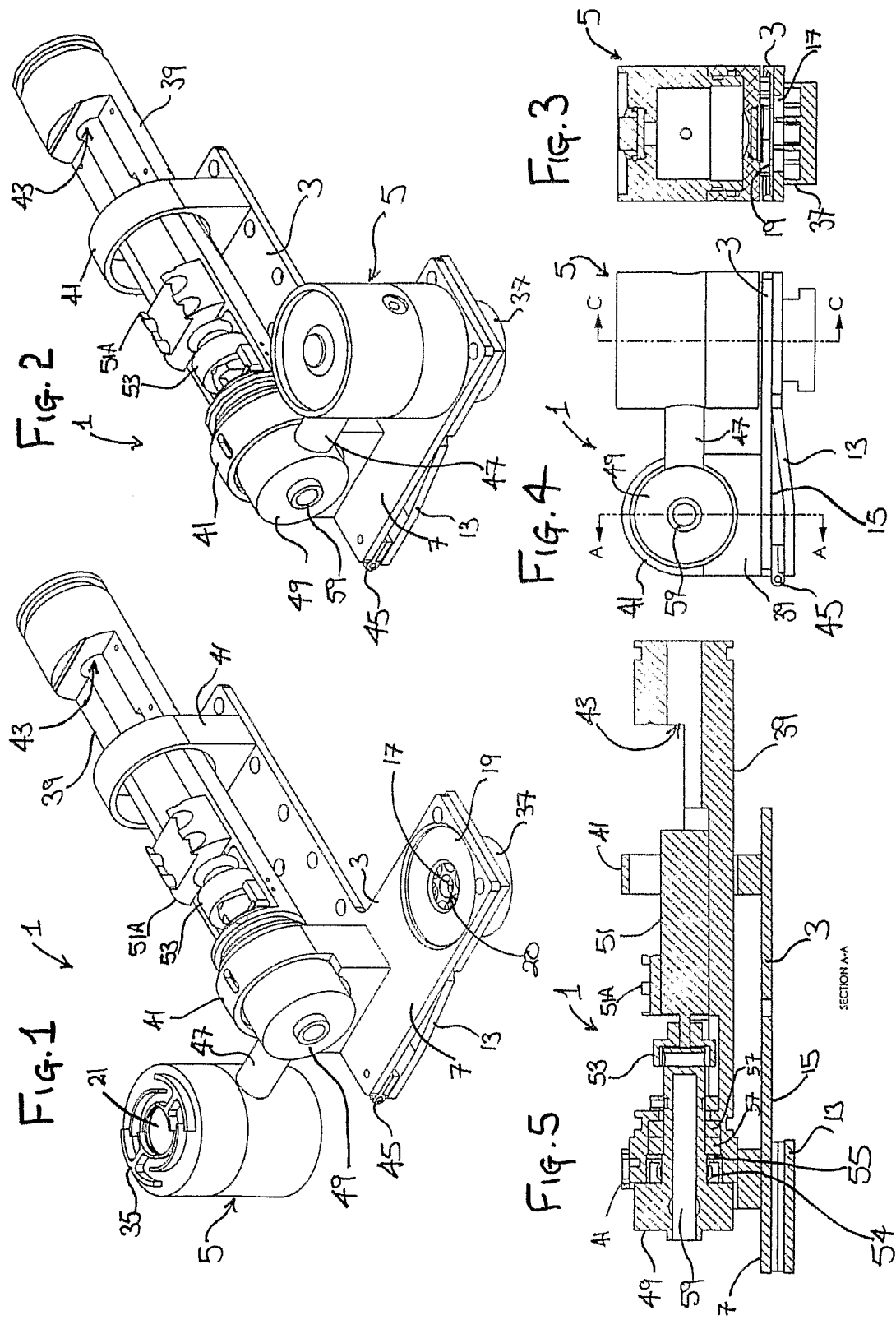

Figure 10
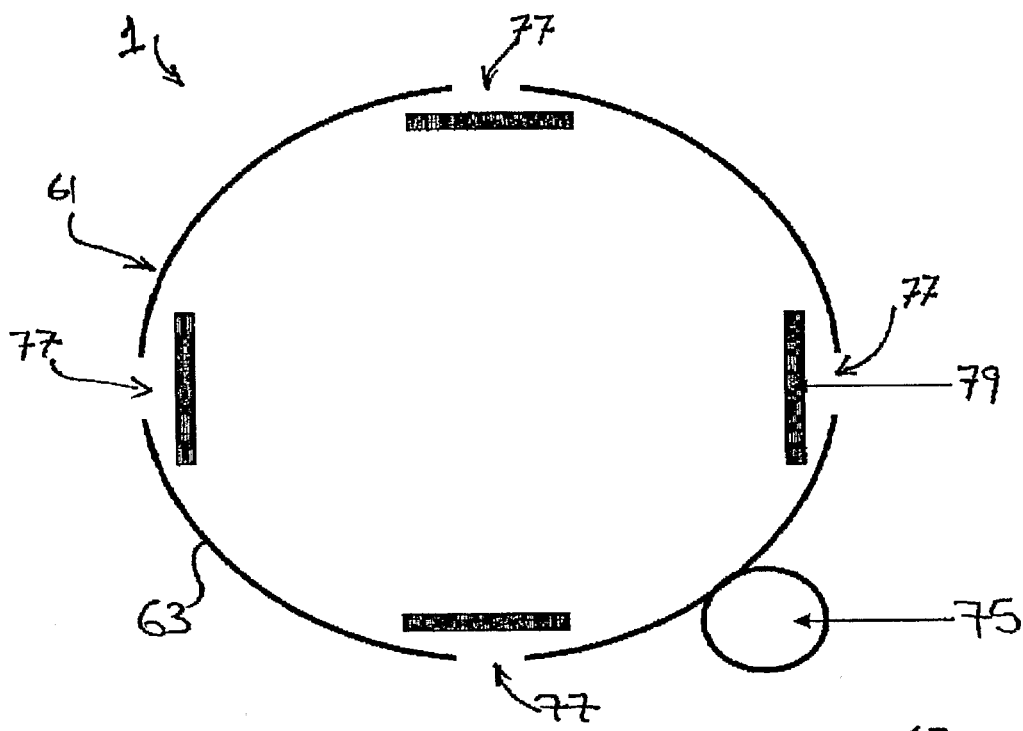
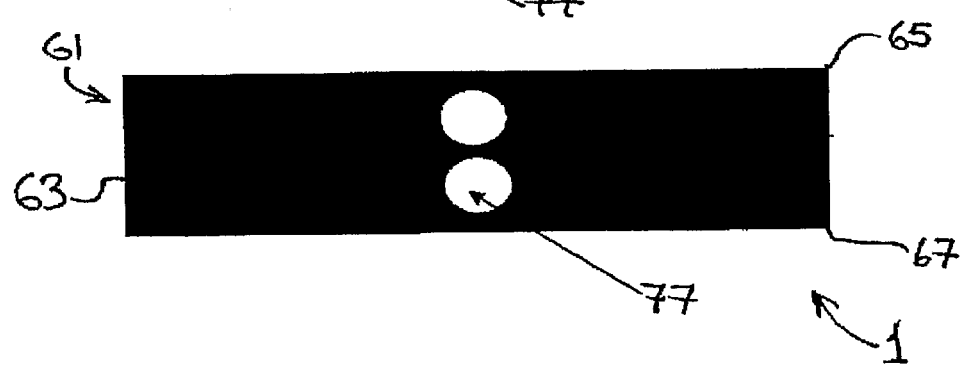
Figure 11

AUTOMATED SHUTTER FOR DARK ACCLIMATING SAMPLES

CROSS-REFERENCE TO RELATED APPLICATIONS

This is a national stage application under 35 U.S.C. 317 and claims priority from International Application No. PCT/AU2009/00295 filed Mar. 13, 2009, the entire contents of which are incorporated herein in their entireties.

FIELD OF THE INVENTION

The invention relates to the dark acclimation of a sample and, in particular, to a shutter apparatus and method for use in dark acclimating a sample.

The invention has been developed primarily for use in making dark acclimated fluorescence measurements of photosynthetic organisms or matter and will be described hereinafter with reference to this particular application. However, it will be appreciated that the invention is not limited to this particular field of use.

BACKGROUND ART

Chlorophyll is a light-absorbing pigment found in all green plants, as well as algae and some bacteria. It is essential for photosynthesis, a process where light energy from the sun is converted to stored chemical energy. When chlorophyll absorbs sunlight it re-emits a small fraction of this light as fluorescence, and variations in the proportion of absorbed energy that is re-emitted can be related to the efficiency of the photosynthetic system. By examining subtle changes in qualities of chlorophyll fluorescence (for example variable fluorescence intensity) in response to specific experimental conditions it can be determined whether photosynthesis is proceeding optimally or whether it has been adversely affected by the environment. In order for the fluorescence signal to be clearly distinguished from background light when measurements are made with ambient light present, the signal is stimulated by a brief typically modulated "excitation" light (typically of order of milliseconds), and the returned fluorescence "emission" signal is read immediately afterwards. Additional lights are often applied to the sample in order to alter its physiological state, thereby extracting more information pertaining to the condition of the sample.

Based on these general principles, numerous chlorophyll fluorescence techniques have been developed and used by many research groups since the mid $20^{th}$ century. These techniques provide information useful in describing the condition of the photosynthetic organism, are used widely in plant and agricultural research and are increasingly used in the commercial sector.

A commonly used technique for directing a beam of excitation light to a sample, and receiving the emission signal from that sample is to use a beam-splitting apparatus, where either the excitation or emission light is directed through a partially mirrored material positioned at 45 degrees to the beam direction. The mirrored material used is generally designed to either allow transmission of the excitation beam and to reflect the emission beam or allow reflection of the excitation beam and transmission of the emission beam. This beam-splitting optical arrangement allows the emission source and the detector to be positioned separately yet in the direct path of the emitted or received beam. While effective, this system requires a relatively precise and stable spatial optical arrangement and a high-quality mirror for it to be effective. This adds to the complexity, cost and physical size of the apparatus.

Within the suite of fundamental fluorescence measurements that can be obtained from modulated fluorometers, the variable fluorescence of temporarily dark-acclimated plant material is generally, but not exclusively, described by the parameter Fv/Fm which remains a vital source of information that describes the photosynthetic system of the plant material measured when it is in a state of partial or complete relaxation, The parameter Fv/Fm is a measure of the efficiency with which light absorbed by the photosynthetic material drives photochemistry; Fv is a measure of the variable fluorescence; and Fm is a measure of maximum fluorescence. Reference is made to publications by Schreiber, U & Falkowski, P and references cited thereby for more detail regarding these measurements.

The parameter Fv/Fm obtained from a dark acclimated sample can then be compared with variable fluorescence values obtained from the photosynthetic system when it is acclimated to ambient light. The protocol for obtaining the Fv/Fm measurement generally requires the sample to be kept in the dark for an interval of at least 10 to 15 minutes prior to taking the measurement. It is generally unnecessary to dark-acclimate the entire plant; rather a small portion of the plant is dark-acclimated (i.e. "sample"). The term "dark-acclimation" is used here to describe the deliberate exclusion of substantially all ambient light from reaching the sample. This includes the exclusion of most or all natural ambient light (e.g. sunlight), artificial ambient light (e.g. overhead lights in a room or enclosure), or any artificial light treatment.

In addition to measuring fluorescence emitted from a photosynthetic sample, useful information pertaining to the physiological quality of the sample can be obtained by measuring the absorbance and reflectance of light; these measurements may also be best made in the dark so that ambient light does not interfere with the sample or measurement. These measurements can also be usefully performed on non-living samples for e.g. colour measurement, and are generally performed using spectrophotometric and colourimetric techniques, although spectrofluorometry has also been used.

The ability to exclude unwanted ambient light from reaching a sample is also necessary when making measurements that require the sample to be exposed to artificial light treatments. By deliberately excluding unwanted ambient light when making these fluorescence measurements one can be certain that the sample is only responding to the artificial light provided. As for dark-acclimation, these measurements require an operator to manually cause the exclusion of external light.

While obtaining measurements from dark-acclimated samples (or from samples where ambient light is excluded and artificial light treatments are applied) is required, equally important is the ability to ensure the sample is exposed to ambient irradiance when not taking measurements or excluding ambient light. Thus the operator needs to be able to ensure the sample is unshaded for some interval of time.

Known methods for temporarily placing a sample in darkness or temporarily excluding the influence of ambient light when conducting fluorescence measurements (and other optical measurements including absorbance transmittance and reflectance) are either to manually exclude all light when conducting the measurement by applying an opaque cover, or when using artificial lights for ambient illumination, simply turn off the lights either manually or automatically when taking the measurements.

The disadvantages inherent in the above methods are that an operator is required to be present whenever the ambient light is to be excluded. This is required because the operator must physically apply opaque covers to the sample to prevent ambient light from reaching the sample, and then remove the cover when the sample is again to be exposed to ambient light. The farmer method can present significant limitations in situations where it is undesirable to have an operator attending the sample for long periods. For example, it would be undesirable for the operator to be required to make regular and frequent measurements over a 24 hour period when the sample is underwater or in a very cold and wet environment. The difficulty in ensuring operator safety under such a sampling regime can be significant and deter the making of any measurements. One disadvantage of the latter method, (i.e. turning off artificial lights), is that this may dark-acclimate the entire sample, and this is generally not desirable.

GENESIS OF THE INVENTION

The genesis of the invention is a desire to provide an automated shutter for dark acclimating a sample which overcomes or substantially ameliorates one or more of the disadvantages of the prior art, or to provide a useful alternative.

SUMMARY OF THE INVENTION

According to a first aspect of the invention there is provided an automated shutter for dark acclimating a sample, said automated shutter comprising:
  a base;
  a head mounted to said base and movable between an open position wherein said head is remote from said base and a closed position wherein said head is closely adjacent to or contiguous with a measurement side of said base; and
  one or more artificial light sources and one or more optical detectors disposed in said head or in said base;
  wherein the sample to be dark acclimated is retained closely adjacent or contiguous with said head when moved into said closed position.

According to another aspect of the invention there is provided an automated shutter for dark acclimating a sample, said automated shutter comprising:
  an enclosure having at least one enclosing side wall extending from a bottom open end upwardly toward an enclosing side wall upper end, and a closure configured to be placed over said top end of said enclosing side wall wherein said enclosure is configured to be placed over a part or all of a sample; and
  one or more artificial light sources and one or more optical detectors disposed within or closely adjacent said enclosure;
  wherein said enclosure or part thereof is configured to be transformed between a substantially optically transparent state and an optically opaque state, and said sample to be dark acclimated is retained in said enclosure.

It can therefore be seen that there is advantageously provided an automated shutter for dark acclimating a sample where the shutter temporarily excludes ambient light from a sample (generally but not exclusively a sample of a photosynthetic organism) such that no operator is required to be present when ambient light is excluded. Further, the automated shutter for dark acclimating a sample advantageously does not employ relatively accurately aligned beam splitters or other relatively accurately aligned optical components.

BRIEF DESCRIPTION OF THE DRAWING

Preferred embodiments of the invention will now be described, by way of example only, with reference to the accompanying drawings in which:
FIG. 1 is a schematic elevated perspective view of an automated shutter in an open position according to a first preferred embodiment of the invention;
FIG. 2 is a schematic view of the automated shutter of FIG. 1 in a closed position;
FIG. 3 is a cut-away side view of a head of the shutter of FIGS. 1 & 2;
FIG. 4 is a front view of the automated shutter of FIG. 2;
FIG. 5 is a cut-away side view of the automated shutter of FIG. 1;
FIG. 10 is a plan view of the shutter of FIG. 9 in a closed configuration;
and
  FIG. 11 is a side view of the shutter of FIG. 9 in a closed configuration.

DETAILED DESCRIPTION

Figure 6:
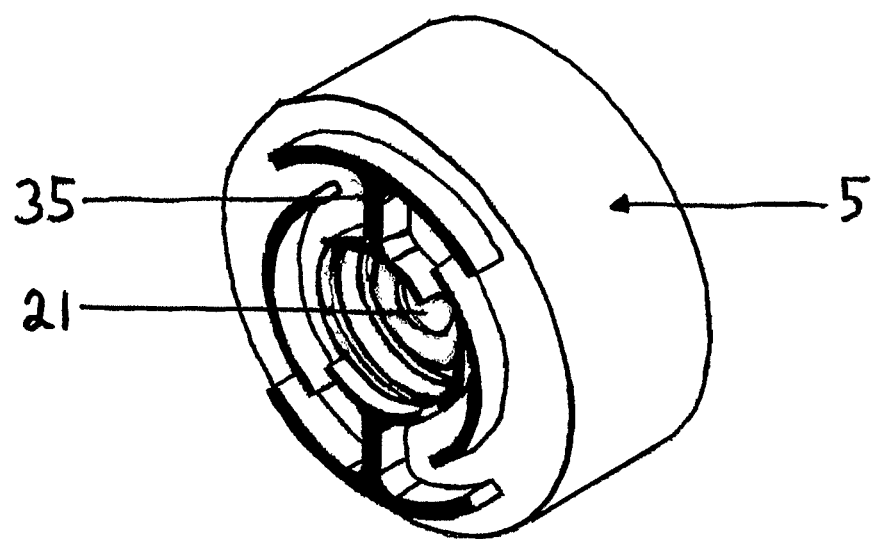
FIG. 6 is a schematic elevated perspective view of the head labyrinthine seal of the head of the shutter of FIG. 1.

Referring to the drawings generally, it will be appreciated that throughout this specification like reference numerals have been used to denote like components. FIGS. 1 to 7, there is shown an automated shutter 1 according to the first preferred embodiment.

FIGS. 1 and 2 are perspective views of the automated shutter 1 for dark acclimating a sample (not illustrated in FIGS. 1 to 7). The automated shutter 1 includes a base 3 and a head 5 mounted to the base 3. The head 5 is moveable between an open position as shown in FIG. 1 where the head 5 is remote from the base 3 and a closed position as shown in FIG. 2 where in the head 5 is contiguous with a measurement side 7 of the base 3.

Figure 7:
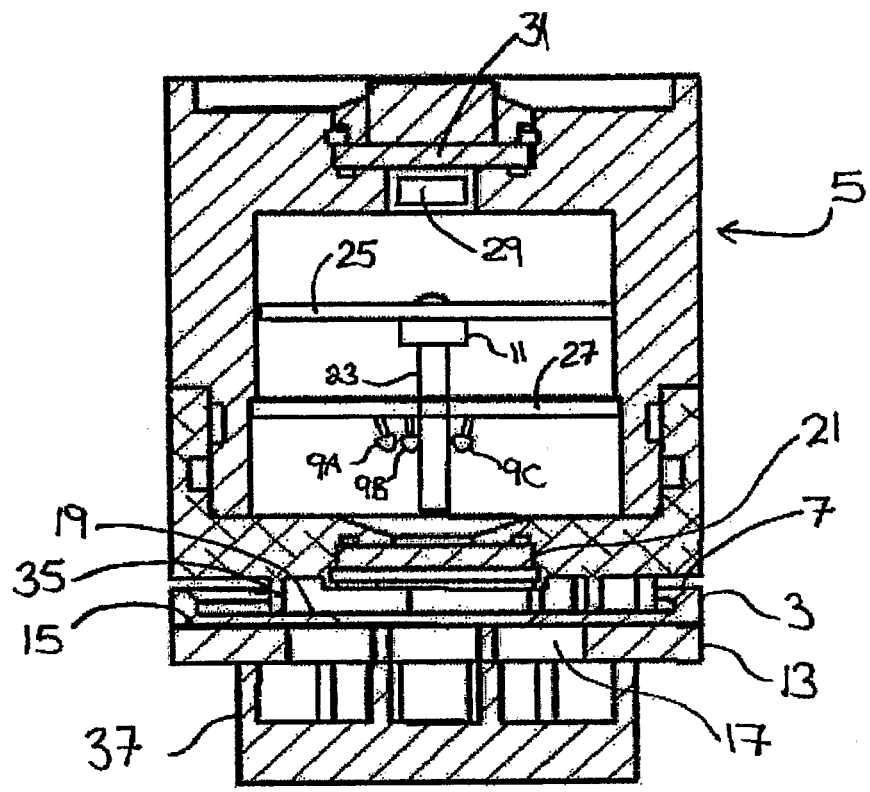
FIG. 7 is a cut-away side view of the head of FIG. 3 having a plurality of artificial light sources, a detector and a light pipe.

The automated shutter 1 includes a plurality of artificial light sources 9 and an optical detector 11 each disposed in the head 5. This is best shown in FIG. 7 and is described below.

The automated shutter 1 is configured to retain a sample to be dark acclimated closely adjacent the head 5 when it is moved into the closed position shown in FIG. 2. The automated shutter 1 further includes a sample clip 13 disposed on the opposite side 15 of the base 3 to the measurement side 7. The clip 13 is configured to retain a sample intermediate the clip 13 and the opposite side 15 of the base 3. The clip 13 includes a plurality of apertures 17 disposed therethrough. The apertures 17 are configured to be disposed adjacent the sample to maintain the sample intermediate opposite side 15. In this way a sample can be illuminated by the artificial light sources 9 disposed in the head 5 and any fluorescence of the sample detected by the detector 11.

The measurement side 7 of the base 3 includes a recessed seat 19 with an aperture 20 within the seat 19. The seat 19 is configured to receive the head 5 when in the closed position as shown in FIG. 2. The recessed seat 19 is configured to provide a substantial light tight seal between it and the head 5. The head 5 includes artificial light sources 9 and detector 11 disposed therein.

As described further below the light sources are positioned adjacent a transmission window 21 disposed in the heads and configured to face the measurement side 7 of the base 3 and particularly the aperture 20 in seat 19 when the head 5 is moved into the closed position. The detector 11 is disposed back from the window 21 and a light pipe 23 extends from the window 21 to the detector 11. The light pipe 23 allows only light incident to the window 21 to be transmitted to the detector 11. This is best shown in FIG. 7 in a schematic cut away side view of the head 5. A pair of circuit boards 25 and 27 are disposed in the head 5. The circuit board 25 has the detector 11 mounted thereto and the light pipe 23 extending therefrom to the window 21. The circuit board 27 is disposed closer to the window 21 than the circuit board 25 and has mounted thereto the artificial light sources 9. The artificial light sources 9 are in the form of light emitting diodes (LED's)and are directed outwardly from the window to illuminate a sample when the head 5 is in the closed position. As best shown in FIG. 7 the circuit board 27 can surround the light pipe 25 so as to provide a light tight enclosure for the detector 23 within circuit boards 25 and 27 and the head 5.

An ambient light sensor 29 is disposed in the head 5 at an opposite end to the window 21. The ambient light sensor 29 is configured to receive ambient light signals through the head 5 which is essential for accurate fluorescence measurements of dark acclimating samples. The light sensor 29 is disposed adjacent an ambient light transmission window 31 which can also act as a plug to allow a non-conductive optically clear oil to fill the inside of the head 5. The use of oil or other suitable fluid, allows the head to be subjected to significant pressures, for example, to be submerged 10's or 100's of meters below the surface in a marine environment. The automated shutter 1 of FIGS. 1 to 7 has been developed for submerged use in measuring fluorescence of photosynthetic materials. This is described further below.

Referring to FIG. 6, there is shown a schematic elevated perspective view of a labyrinthine head seal 35 disposed on an end of the head 5 and about the transmission window 21. The labyrinthine seal 35 is configured to be received in the recessed seat 19 on the measurement side 7 of the base 3.

The labyrinthine seal 35 is configured to allow air or fluid flow therethrough whilst excluding ambient light. The labyrinthine seal 35 is most preferably formed from a non-reflective material that is slightly deformable to provide good contact between the seal 35 and the recessed seat 19.

Although not clearly shown in the drawings and perhaps best seen in FIGS. 3 and 7, an underside of the clip 13 also includes a labyrinthine seal 37 to allow water or air flow therethrough and through the apertures 17 in the clip 13 to have water or air flow thereby. It will be appreciated that the labyrinthine seal 37 allows the water or air flow whilst restricting the ingress of any ambient light.

Figure 8:
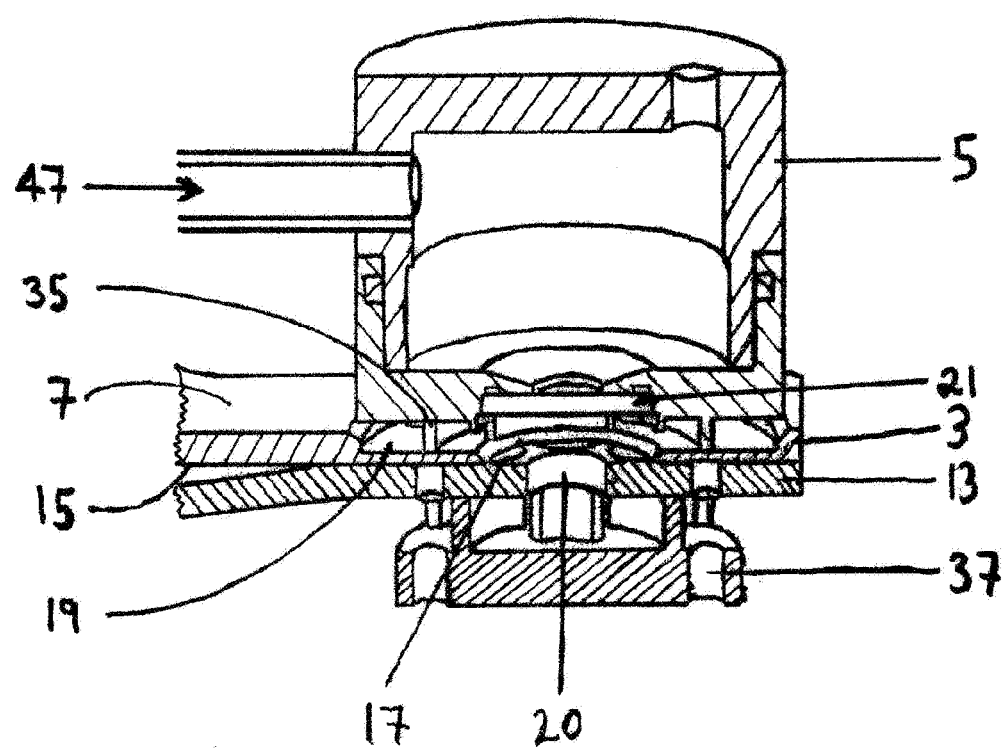
FIG. 8 is a schematic elevated perspective view of an alternative embodiment of the head of FIG. 3.

As best shown in FIG. 8 which provides an alternative embodiment to the head used in the embodiment of FIGS. 1 to 7 and which does not include an ambient light detector but instead includes a threaded sump plug aperture to receive oil to fill the head 5 as described above. In this embodiment but similarly with the first embodiment, it can be seen that water or air entering the labyrinthine seals 35, 37 is capable of flow through the apertures 17 if the sample does not completely cover them. It will be appreciated in other embodiments of the invention, not illustrated, that the labyrinthine seals can be connected to one or more air or liquid pumps to force flow thereof though the labyrinths. In any event, fluid flow through the labyrinths advantageously reduce the effects of conducting dark acclimated measurements on the samples. This is described further below.

It can be seen that the movement of the head 5 between the open position shown in FIG. 1 and the closed position shown in FIG. 2 can provide an automated shutter. It is noted the preferred embodiments are configured to dark acclimate marine or terrestrial photosynthetic organisms in the form of plant matter, or water born micro-organisms, for example.

It can be seen that the head 5 in the open position it does not shade or otherwise obstruct or interfere with a sample retained by the clip 13 until moved into the closed position and ambient light is excluded. It will be appreciated that electronic components configured to control the automated shutter 1 to allow the taking the fluorescence or optical measurements are incorporated into the head 2 and a body 39. The body 39 is shown to be clamped to the base 3 by means of clamps 41. It will be appreciated that the body 39 in the drawings is shown without an external waterproof cover. An aperture 43 is provided at end of the body 39 distal from the head 5 to provide electrical cable feed through.

The automated shutter 1 of the preferred embodiment of FIGS. 1 to 7 is water resistant allowing measurements to be made under water for hours or days before an internal power supply (not illustrated) is exhausted, or for any predetermined longer period of time if electrical power is supplied via cable feed 43.

The cavity formed within body 39 is sealed as noted above. O-ring seals are disposed about transmission window 21 and window 31 to prevent water ingress into the head 5. The clip 3 is mounted to the opposite side 15 of the base 3 by means of a hinge 45. The labyrinthine seal 37 is disposed on a side of the clip 13 facing away from the base 2. An area of the clip 3 above the labyrinthine seal 37 including the plurality of apertures 19 is best shown in FIGS. 1, 3 and 7. It will be appreciated that additional resilient bias means such as elastic bands can be disposed around the clip 13 and the base 3 to control the pressure between the clip 13 and the base 3 when a sample is retained.

It will be appreciated that the labyrinthine seals 35 and 37 allow air or water to be released when the head 5 is engaged with recessed seat 19.

The head 5 is rotatably mounted to one end of the body 39 via a rotating arm 47. The arm 47 is connected at a base 49 to the body 39. The base 49 is interconnected with a motor/gearbox assembly 51 retained to the body 39 by means of a clamp 51A. Intermediate the base 49 and the motor/gearbox assembly 51 is a clutch mechanism 53 configured to disengage the motor/gearbox assembly 51 from the base 49 in response to a predetermined torque to prevent damage to the motor/gearbox assembly 51 or any shaft interconnecting the motor/gearbox assembly 51 and base 49.

In the embodiments of FIGS. 1 to 7, electrical wiring extends from the head 5 through arm 43 into the base 49 and through into the body 39. The base 49 is rotatably mounted to the body 39 by means of two seals 53 and 55. As best shown in FIG. 5, a lip seal 53 is provided intermediate the base 49 and body 39 to prevent fluid or air ingress therein. A secondary seal 55 is disposed substantially and parallel with the seal 53. A pair of bearings 57 are used to mount a drive shaft 59 connecting the clutch 53 and the base 49. A motor drive shaft 61 is disposed intermediate the clutch 53 and motor/gearbox assembly 51 positionally shown schematically shown in FIG. 5 disposed under clamp 51A.

Referring to FIG. 7 particularly, reference is again made to the artificial the light source 9 in the head 5. Three LED's are provided as follows:

LED 9A provides a relatively bright white artificial illumination;
LED 9B provides a far infrared light having a wavelength of the order of 735 nm; and
LED 9C is a blue diode.

It will be appreciated that white LED 9A is a higher powered blue LED than the blue LED 9C but diode 9A has a phosphor coating which produces a white light.

In use, head 5 is moved to the open position for a period of about 1 to 1.5 hours. The head 5 is then closed for approximately 10 to 15 minutes where a fluorescence measurements of a sample retained in the clip are made every two or three minutes or some other preferred non-uniform interval whilst the head 5 is in the closed position. This process is repeated over a predetermined period of time, usually one to two days. It will be appreciated that ambient light is continually monitored via light sensor 29 through window 31.

Typically, the blue LED 9C is relatively low power and provides approximately 6 microsecond long pulses over a 800 microsecond period and provides ten fluorescence measurements intermediate the firing of diode 9C. This procedure is repeated 10 times before and 10 times during light emission from diode 9A, however, any preferred repetition rates can be employed.

It will be appreciated by those skilled in the art that alternative fluorescence excitation and measurement protocols can also be followed using the optical and electronic arrangement of the preferred embodiment including but not limited to those commonly known as fast repetition rate fluorometry or polyphasic fluorescence rise.

The fluorescence measurement from a sample retained in the clip with the head 5 in the closed position are made during the excitation of the LED's providing a pico or nano-second response of fluorescence. A filter (not illustrated) to block blue light is disposed intermediate the detector 11 and the light pipe 23 so that only fluorescence is measured as this is typically in the infrared or red end of the spectrum. The white LED 9A is then actuated to saturate the sample retained by the clip 13 with essentially white light whilst maintaining operation of the blue LED 9C. The use of the blue LED can provide a base line for analysis of measured fluorescence results.

The red LED 9B is then activated to induce reduction to a base line in a photosynthesis mechanism under investigation. It will be appreciated that the lenses of the LED's 9 are directed through the transmission window 21 to focus substantially on a point equally distant from the transmission window 21 where the sample is positioned by clip 13. A light diffusing element can be disposed intermediate the ambient light sensor 29 and the ambient light to diffuse the ambient radiation prior to transmission through the window 31. It will be appreciated that a lip can be provided on such a diffusing disc so as to improve the efficiency measured irradiance of the ambient light when the sun is low on the horizon.

As described above, the body 39 includes control electronics and means for retaining or transmitting data acquired from the automated shutter 1. Controlling, electronics operate the automated shutter 1 as well as control the measurement of irradiance and temperature and the operation of the motor/gearbox assembly 51 controlling the movement of the head 5. An external electronic device (data logger) is connected through aperture 43 and the body 39 to external power and/or electrotonic control and/or communication equipment. The data logger provides data logging functions as well as providing power and controlling functions that are preset by an operator by linking the data logger to an external computer. When commanded by the data logger, the motor/gearbox assembly 51 is activated to rotate base 49 and arm 47 and head 5 to move head 5 into the closed position against recessed seat 19. A switch mechanism (not illustrated) is provided to remove power to the motor when the head 5 is moved into the closed position for dark acclimating a sample retained by the clip 13.

As preferred, the head 5 may then be controlled to commence making fluorescence measurements or provide artificial light to the sample or both. On command and after a predetermined period of time, the motor/gearbox assembly 51 is activated and head 5 moved into the open position allowing the sample to be fully exposed to ambient irradiance whilst not providing any shading by the head 5. Of course it will be appreciated that the motor/gearbox assembly 51 can be activated and measurements taken as desired.

It will be appreciated that the preferred embodiment of FIGS. 1 to 7 is designed to operate submerged in water to pressures of at least three bar as follows and in the air. The automated shutter 1 preferably operates for at least a 24 hour period and preferably a 36 hour period on a single integrated power supply, however, it will be appreciated from the above that any external power supply can be provided if desired.

Figure 9:
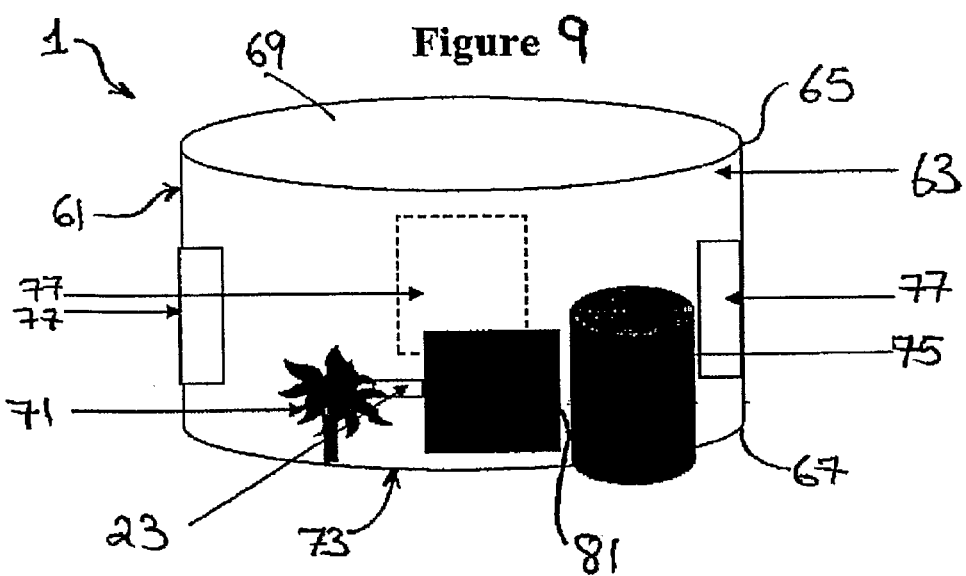
FIG. 9 is a schematic representation of an automated shutter in an open configuration according to another aspect of the invention.

Referring now to FIG. 9, there is a schematic representation of an automated shutter 1 in an open configuration according to another preferred embodiment. FIG. 10 is a schematic plan view of the automated shutter of FIG. 9 and FIG. 11 is a side view of the automated shutter 1 of FIG. 9. In this embodiment, the automated shutter 1 is configured for dark acclimating a sample and includes an enclosure 61 having at least one enclosing side wall 63 formed of a part cylinder extending from a bottom end 65 upward a predetermined distance toward an upper end 67. A closure 69 is configured to be placed over the upper end 67 of the enclosing side wall 63. The enclosure 61 is configured to be placed part or all of a photosynthetic sample.

The enclosing side wall 63 and closure 69 are configured to be electrically stimulated to be transformed between a substantially optically transparent state as shown in FIG. 9 and an optically opaque state as shown in FIGS. 10 and 11. The sample to be dark acclimated is denoted 71 and is shown as a little tree for illustration purposes. The sample 71 is retained in the enclosure 61 in a predetermined position. In the embodiment of FIG. 9, the bottom end 65 of the enclosing side wall 63 includes a base 73 and an entrance (not illustrated) to receive sample 71. The enclosing side wall 63 and closure 69 are formed from a liquid crystal display material such that application of predetermined electrical power causes the side wall 63 and closure 69 to transform between optically clear and optically opaque states. Whilst a liquid crystal type material is suitable for providing optically transparent and opaque conditions, any preferred light modulator capable of transformation from optically clear to optically opaque states can be used. Although not clearly shown in FIG. 9, the sample 71 is retained in a fixed location in the enclosure 61 by means of a clip or clamp device to maintain the position and orientation of the sample 71.

Power and electronic control of the automated shutter 1 is provided by a battery pack and controller 75 disposed externally to the enclosure 61. The enclosure 61 includes two or more light traps 77 allowing water and/or air to pass freely through the chamber preventing the passage of ambient light into the enclosure 61. Baffles 79 are provided to allow light traps 77 to be selectively closed. The baffles can be manually or electrically operated as desired. It will be appreciated that closing the baffles 79 would allow measurement of dissolved gas concentration in the medium in the enclosure 61. This can used to calculate metabolic rates of oxygen and/or carbon dioxide flux.

A fluorescence or optical measurement is made by either a stand alone fluorometer or optical device 81 disposed within the chamber and directed to perform measurements on the sample 71. It will be appreciated that the fluorometer or optical device 81 can include a clip or retaining device for the sample 71 if desired so that the sample 71 is orientated relative to the fluorometer or optical device 81. The fluorescence measurements are made with the enclosure 61 in an optically opaque state in the same manner measurements are made with the embodiment of the shutter 1 shown in FIGS. 1 to 7 in the closed position.

It is this preferred embodiment rather than moving the head 5 to provide dark acclimation, the enclosure 61 is transformed to be optically opaque. This embodiment also advantageously removes the need for operator intervention whenever ambient light is to be excluded from the sample 71 and a measurement made. The automated shutter 1 of FIG. 9 can also be used in air or when submerged. It will be further appreciated that the fluorometer or optical device 81 can be movable within the enclosure or be movable from external to the enclosure to within the enclosure for the purposes of making measurements. This is not illustrated in the drawings and is applicable to other preferred embodiments of the invention.

It will be appreciated that in other embodiments of the invention, not illustrated, other means for making the enclosure side wall 63 and/or closure 69 optically opaque can be effected in any desired manner. For example, a cross-polariser arrangement where two substantially parallel polarisers are disposed opposite each other and extend substantially parallel with each other can be provided. In order to cause optical opacity, one of the pair of polarizers is rotated by 90 degrees by means of a motor or the like to restrict ambient light from entering the chamber.

It will be appreciated also that one of the problems encountered when placing a biological sample in a fixed position for an extended interval is the influence of the sample holding apparatus on the behaviour of the sample itself. The preferred embodiments advantageously provide a labyrinth or light trap arrangement that acts to exclude potentially all ambient light from reaching the sample, while enabling the surrounding medium typically water or air, to pass by the sample. This is particularly important for the continued removal of waste gases and products as well as the replenishment of essential gases such as oxygen or carbon dioxide and nutrients to the sample.

In some instances, the operator may wish to prevent the removal of waste gases from the enclosure 61 for the purpose of measuring the flux of these gases from the sample 71. In these instances, the baffles 79 may be maintained in a closed position for some or all of the time.

A further deficiencies of the prior art advantageously addressed by the preferred embodiments of the present invention include removal of the use of beam splitting optical arrangement where the emission and excitation beams are passed through or reflected off a beam splitting device enabling the beams to be generated and received at different locations. The preferred embodiments of the present invention eliminate any requirement for such an optical arrangement by orienting the LED's 9 and the detector 11 to a focal point that is co-located by the sample. This arrangement is relatively simple, inexpensive and particularly effective.

Yet a further deficiency of the prior art addressed by the preferred embodiments of the present invention involve the removal of the need to use devices such as "leaf clips" that prevent the flow of air or water passing the sample whilst excluding ambient light from reaching it. The labyrinthine seals 35 and 37, for example, advantageously trap light whilst allowing fluid or air pass over or pass the sample and at the same time excluding ambient light from the sample.

The foregoing describes only one embodiment of the present invention and modifications, obvious to those skilled in the art, can be made thereto without departing from the scope of the present invention.

The term "comprising" (and its grammatical variations) as used herein is used in the inclusive sense of "including" or "having" and not in the exclusive sense of "consisting only of".

The invention claimed is:

1. An automated shutter for temporarily dark acclimating a sample in a surrounding medium from ambient light, said automated shutter comprising:
    a base;
    a head mounted to said base and movable between an open position wherein said head is remote from said base and a closed position wherein said head is closely adjacent to or contiguous with said base; and
    one or more artificial light sources and one or more optical detectors disposed in said head or in said base;
    wherein the sample to be dark acclimated is retained closely adjacent or contiguous with said head when moved into said closed position and the sample is exposed to the surrounding medium at least when the shutter is in the open position.

2. An automated shutter according to claim 1, wherein said head is rotatably mounted for movement between said open and closed positions, and wherein said one or more light sources and detectors are disposed in said head adjacent a window disposed in said head such that said window faces a measurement side of said base when said head is in said closed position.

3. An automated shutter according to claim 2, comprising a sample clip disposed on an opposite side of said clip to said measurement side, said clip configured to retain said sample intermediate said clip and said opposite side of said base, wherein said base includes one or more apertures such that said sample can be illuminated by said artificial light sources and any fluorescence thereof detected by said detectors.

4. An automated shutter according to claim 3, wherein said measurement side of said base includes a recessed seat configured to receive said head in said closed position and provide a substantially light tight seal therebetween.

5. An automated shutter according to claim 4, wherein said clip includes one or more apertures and a clip labyrinthine seal configured to be disposed over said apertures on said clip on a side of said clip facing away from said sample and said base wherein said clip labyrinthine seal includes a path configured to allow fluid to flow therethrough and over one side of said sample with the other side of said sample disposed against said apertures in said base.

6. An automated shutter according to claim 5, wherein said head includes a head labyrinthine seal disposed at least about said head window and extending a predetermined distance from said head, said head labyrinthine seal including a path configured to allow fluid to flow therethrough and over and/or through said base apertures when said head is in said closed position, wherein said head seal is configured to form a substantially light tight seal with said recessed seat in said base.

7. An automated shutter according to claim 1, including an ambient light sensor disposed in or on said head and configured to provide an indication of ambient light levels when said head is in said open or closed positions or a position therebetween.

8. An automated shutter according to claim 2, comprising a light pipe disposed in said head and extending from said window to said detectors spaced apart therefrom, wherein said artificial light sources are spaced apart from said light pipe and directed to provide illumination outwardly through said window.

9. An automated shutter according to claim 3, including a remotely actuatable and programmable electronic controller configured to control: movement of said head between said open and closed positions; operation of said artificial light sources and detectors; storage and/or transmission of data acquired by said detectors; and data indicative of said operation of said artificial light sources and detectors.

10. An automated shutter according to claim 1, comprising a motor and associated gearbox assembly and clutch configured to move said head between said open and closed positions.

11. An automated shutter according to claim 10, including an electrical power supply disposed adjacent said motor, disposed in said head or disposed remotely therefrom and in electrical communication therewith.

12. An automated shutter according to claim 1, and configured to move said head from said open position into said closed position and to selectively illuminate said sample and measure any one or more of reflectance, transmittance, absorbance or fluorescence of said sample at pre-defined intervals and move said head to said open position.

13. An automated shutter according to claim 6, wherein said base or head labyrinthine seals can be selectively closed to the flow of fluids therethrough, or have fluid selectively pumped therethrough.

14. An automated shutter according to claim 1, wherein said head is filled with a non-conductive optically clear oil.

15. An automated shutter for temporarily dark acclimating a sample in a surrounding medium from ambient light, said automated shutter comprising:
    an enclosure having at least one enclosing side wall extending from a bottom open end upwardly toward an enclosing side wall upper end, and a closure configured to be placed over said top end of said enclosing side wall wherein said enclosure is configured to be placed over a part or all of a sample; and
    one or more artificial light sources and one or more optical detectors disposed within or closely adjacent said enclosure;
    wherein said enclosure or part thereof is configured to be transformed between a substantially optically transparent state and an optically opaque state, and said sample to be dark acclimated is retained in said enclosure and is exposed to the surrounding medium at least when the enclosure is in a the optically transparent state.

16. An automated shutter according to claim 15, wherein said closure or part thereof is configured to be selectively transformed between an optically transparent state and an optically opaque state.

17. An automated shutter according to claim 15, wherein said closing side wall bottom end includes an enclosing base having an entrance to receive said sample.

18. An automated shutter according to claim 15, wherein said artificial light sources and optical detectors are disposed within a moveable measurement head disposed within said enclosure and mounted to said enclosure.

19. An automated shutter according to claim 15, wherein said enclosure or part thereof is configured to be transformed between optically clear and opaque in response to an electrical signal.

20. An automated shutter according to claim 15, wherein said enclosing side wall and said closure are formed from one or more liquid crystal display elements or light modulator.

21. An automated shutter according to claim 15, having a power supply and shutter controller disposed external to said enclosure.

22. An automated shutter according to claim 15, having a sample clip disposed within said enclosure and configured to retain said sample in a predetermined location and orientation within said enclosure.

23. An automated shutter according to claim 18, wherein said measurement head is configured to move between a disengaged position and an engaged position and to selectively illuminate said sample and measure any one or more of reflectance, transmittance, absorbance or fluorescence of said sample at predefined intervals and move said head to said disengage position.

24. An automated shutter according to claim 15, wherein said enclosure includes one or more vents having baffled light traps wherein said baffles are movable to close said vents.

* * * * *